United States Patent [19]

Haschke

[11] Patent Number: 4,491,128
[45] Date of Patent: Jan. 1, 1985

[54] METHOD OF MAKING A SURGICAL CAST WITH WINDOW

[76] Inventor: Paul C. Haschke, 8288 W. Roosevelt Rd., Forest Park, Ill. 60130

[21] Appl. No.: 409,734

[22] Filed: Aug. 19, 1982

[51] Int. Cl.³ .............................................. A61F 5/04
[52] U.S. Cl. ............................... 128/91 R; 128/419 F
[58] Field of Search ............... 128/91 R, 132 R, 154, 128/419 F, 92 A, 82, 83, 82.1

[56] References Cited

U.S. PATENT DOCUMENTS

| | | | |
|---|---|---|---|
| 679,918 | 8/1901 | Shears | 128/154 X |
| 703,290 | 6/1902 | Mulford | 128/154 |
| 2,367,690 | 1/1945 | Purdy | 128/132 R |
| 2,855,922 | 10/1958 | Schroeder | 128/91 R |

FOREIGN PATENT DOCUMENTS

| | | | |
|---|---|---|---|
| 1914096 | 10/1970 | Fed. Rep. of Germany | 128/154 |
| 701472 | 3/1931 | France | 128/154 |
| 1527887 | 6/1968 | France | 128/154 |
| 288220 | 7/1927 | United Kingdom | 128/154 |

Primary Examiner—John D. Yasko
Attorney, Agent, or Firm—E. J. Berry

[57] ABSTRACT

A surgical cast for use in treating bone fractures, especially fractures with pins that extend to a pin-site area, includes an opening at the pin-site area and a window that aligns with the opening. The window has a surface that projects away from the pin-site and defines a clearance space between the cast and the pin-site to avoid any rubbing of the pins by the cast. The window also furnishes clearance at the pin-site for terminal connections to a bone growth stimulator.

2 Claims, 5 Drawing Figures

METHOD OF MAKING A SURGICAL CAST WITH WINDOW

BACKGROUND OF THE INVENTION

This invention relates to surgical casts for a body surface and more particularly, to a surgical cast formed with an opening that contains a window.

Surgical casts are well know for their use in immobilizing a fracture to enable the fracture to properly fuse. It is also well known that the immobility furnished by a cast is not absolute and therefore most surgical casts can move slightly relative to the body surface that is cast. Although this movement is generally miniscule, it can lead to problems in certain instances.

For example, when a fractured bone such as a tibia, femur or humerus is set, small pins are often inserted through the skin at the vicinity of the fracture with one end of each pin being located at the fracture and an opposite end thereof being located approximately at skin level in an area known as the pin-site. Although the pins help to stabilize the fracture and promote healing, rubbing of the cast at the pin-site causes undesirable movement of the skin against the pins which can chafe, irritate and infect the area around the pin-site.

It has been found that a small amount of electric current applied to the area around the fracture also helps to promote healing by stimulating and accelerating the bone fusion process. This discovery has led to the development of bone growth stimulators that furnish a predetermined amount of current to the fractured area by, for example, a connection to the pins at the pin-site. However, the connecting structure at the pin-site can even further compound the problem of irritation or infection due to rubbing of the cast at the pin-site.

Unfortunately, such movement of the cast relative to the skin at the pin-site, while potentially troublesome, cannot be effectively avoided because most attempts to provide a tight-fitting cast can cause a more insidious problem of circulatory obstruction.

It is thus desirable to provide a cast for the body surface which eliminates rubbing at the pin-site and maintains a sterile condition at the area of the pins whether or not a bone growth stimulator is connected to the pin-site area.

SUMMARY OF THE INVENTION

Among the several objects of the invention may be noted the provision of a novel surgical cast for a body surface, a novel surgical cast for a body surface which incorporates a window, a novel surgical cast for a body surface having an opening covered by a window wherein the surface portions of the window project away from the opening, a novel window for a surgical cast and a novel method for making a surgical cast.

Other objects and features of the invention will be in part apparent, and in part pointed out hereinafter.

The present invention relates to a novel surgical cast for a body surface having an opening covered by a window at a selected portion of the body surface to prevent rubbing contact between the selected body surface portion and the cast.

In a preferred embodiment of the invention, the cast is formed with an opening at a pin-site area where pins extend from a bone fracture to skin level. The opening in the cast is covered and essentially sealed by a window member which is supported on an underlayer of the cast, for example, and held in place by an overlayer of cast material which secures the periphery of the window member to the underlayer. The window member has a surface that is shaped to project away from the opening in the cast and preferably includes tabs that facilitate incorporation of the window member into the cast.

Thus, the window member and the cast combine to form an enclosed space around a selected portion of the body surface at a predetermined location on the cast. The selected body surface portion is not contacted by the inner surface of the cast or the window member and thus is not subject to rubbing against the cast. Furthermore, since the selected body surface portion is completely sealed by the window member and the cast material, the sterility of the enclosure is assured.

In addition, if use of a bone growth stimulator is desired, the window member affords sufficient clearance for the pin ends and their connection to the bone growth stimulator to avoid any rubbing of the selected body surface portion at the area of the pin-site. Thus, the problem of chafing, rubbing, irritation and infection at the pin site due to relative movement between the surgical cast and a body surface at the pin-site is solved.

In making the cast in accordance with the invention, a cloth padding and/or other suitable underlayer means is placed onto the body surface at the area of the fracture. However, the underlayer is omitted at the pin-site, thus leaving an open area of predetermined size. A bone growth stimulator is connected at its cathode to the pins extending from the fracture, the anode of the stimulator being placed against the skin at a predetermined distance away from the fracture. A window member sized to cover the pin-site area is supported on the underlayer that surrounds the pin-site. Moistening cast material such as plaster bandage, is then placed on the underlayer and around the periphery of the window member such that the plaster bandage, upon curing, holds the window member in position on the underlayer.

The invention accordingly comprises the constructions hereinafter described, the scope of the invention being indicated in the following claims.

BRIEF DESCRIPTION OF THE DRAWINGS

In the accompanying drawings in which various embodiments of the invention are illustrated.

DESCRIPTION OF THE PREFERRED EMBODIMENTS

Figure 1:
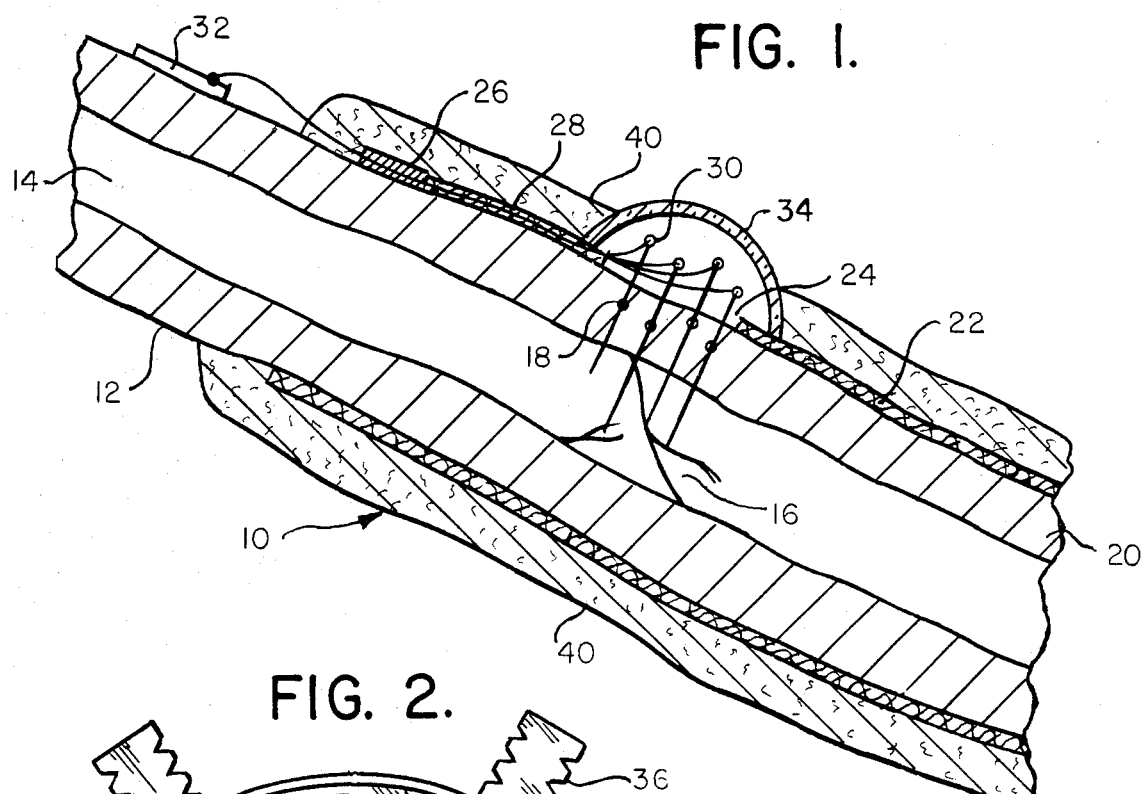
FIG. 1 is a simplified schematic sectional view of a surgical cast incorporating one embodiment of the invention.

Referring to the drawing, a surgical cast is generally indicated by the reference number 10 in FIG. 1. The cast 10 is disposed around a limb 12 containing a bone 14 with a fracture indicated at 16. A plurality of pins 18 extend from the fracture 16 to a skin layer of the surrounding tissue 20 or project slightly beyond the skin layer at an area known as the pin-site.

The cast 10 comprises an underlayer 22 of bandage, padding, stockinet or sheet wadding, the constituents of which are well known in the art. The underlayer 22 is discontinuous at the pin-site thus defining an opening 24.

A bone growth stimulator such as the Zimmer Bone Growth Stimulator manufactured by the Zimmer Company of Warsaw, Ind., 76580, is arranged on or in the underlayer 22 and includes a conduit 28 having cathode connectors 30 that connect to the pins 18 in any suitable known fashion. The stimulator 26 also includes an anode pad 32 placed on the skin a predetermined distance from the fracture 16.

A window member 34, formed of shatter-proof glass or clear or opaque plastic, preferably capable of withstanding an autoclaving process, is disposed on the underlayer 22 in alignment with the opening 24 so as to cover the opening 24. The window member 34 includes a dished window surface having a dome-like peaked portion and is so formed that substantially the entire window surface projects away from the opening 24.

Figure 2:
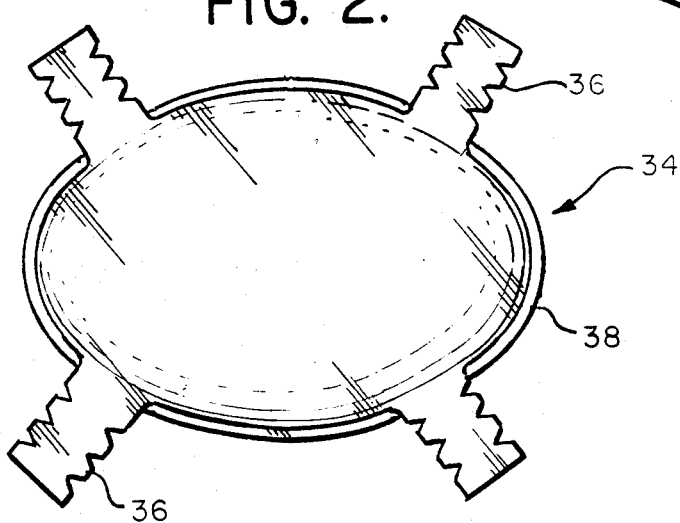
FIG. 2 is a top plan view of the window member used in the cast.
Figure 3:
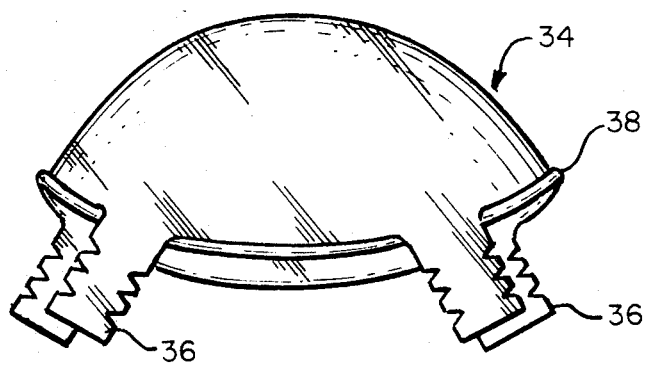
FIG. 3 is a side view thereof.

Referring to FIGS. 1, 2 and 3, the window member 34 includes tabs 36 formed of any suitable flexible, bendable, non-corrosive material that is compatible with the material comprising the surgical cast 10. The tabs 36 are bonded or otherwise secured to the window periphery and facilitate incorporation of the window member into the cast 10. The tabs 36 also prevent accidental removal of the window member 34 from the cast 10.

The periphery of the window member 34 has a rounded lip portion 38 that enhances the attachment of member 34 to the cast 10 and promotes a comfortable fit of the window member around the body surface portion enclosed by the window member 34.

One or more layers of moldable casting material 40, such as moistened plaster bandage, are then wrapped around the underlayer 22, the tabs 36 and the lip portion 38 of the window member 34 to secure and firmly position the window member 34 on the underlayer 22 when the casting material 40 is cured.

The space defined within the window member 34 is substantially sealed from the outside and a sterile condition within such a space, if originally present, can thus be maintained. The distance of the window surface from the pin-site area, especially the pins 18 and the cathode connector 30, provides sufficient clearance to ensure that no rubbing, chafing or other similar irritation will result at the pin-site due to relative movement between the cast and the selected body surface portion at the pin-site. The likelihood of infection at the pin-site due to rubbing by the cast 10 is thus minimized. Under this arrangement, the bone growth stimulator 26 provides a small microamp current, such as 60–80 microamps, to the fracture via the pins 18 to accelerate the bone fusion process by stimulating bone growth.

Figure 4:
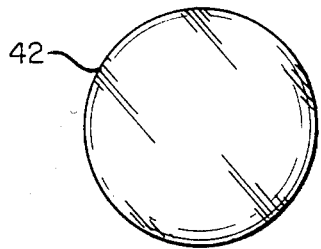
FIGS. 4 and 5 show different embodiments of window members that can be used in the cast of FIG. 1.
Figure 5:
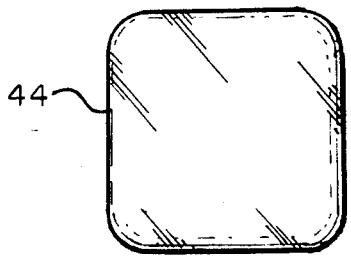

Window members of various size and shape, such as the circular-shaped member 42 of FIG. 4, or the rectangular-shaped member 44 of FIG. 5, can be used with cast 10 depending on the contour of the body surface and the size of the pin-site area. The tabs and lip portion of the window members 42 and 44 have been omitted for the sake of simplicity.

If desired, the window members 34, 42 and 44 can be used at the pin-site without a bone growth stimulator, since the presence of the window member will prevent irritation that occurs if the pin ends are rubbed by a surgical cast.

In view of the above, it will be seen that the several objects of the invention are achieved and other advantageous results attained.

As various changes can be made in the above constructions and methods without departing from the scope of the invention, it is intended that all matter contained in the above description or shown in the accompanying drawings shall be interpreted as illustrative and not in a limiting sense.

What is claimed is:

1. A method of making a cast for a body surface used in combination with a bone growth stimulator, comprising, placing a non-rigid underlayer material onto the body surface, except at a selected body surface portion such that the omission of underlayer material at the selected body surface portion defines an opening in said underlayer, selecting a window member slightly larger than said opening surrounding the opeing to enable the window member to extend across the opening to cover the opening, the surface of the window member being so formed that a substantial portion of the entire window surface projects away from the opening, and layering uncured moldable casting material onto the underlayer material and onto the periphery of said window member, and allowing the casting material to cure to form a rigid overlayer that holds the window member in position over the selected body surface portion, wherein the said body surface includes a bone fracture having pins to set the bone, the pins extending to the selected body surface portion and the bone growth stimulator has means for making electrical communication with the bone including an electrical conduit, the method further including extending the electrical conduit to the opening and connecting the conduit to the pins at said selected body surface portion, the window member and the opening in said underlayer providing an enclosed protective space for said connection, and precluding any rubbing of said cast against said pins or the conduit connection to said pins.

2. The method of claim 1 where the electrical conduit is extended to the opening and connected to the pins prior to disposing the window member over the opening and layering the uncured cast material onto the underlayer.

* * * * *